United States Patent [19]

Sisti et al.

[11] 4,286,456
[45] Sep. 1, 1981

[54] GAS CHROMATOGRAPHIC CHAMBER

[75] Inventors: Giorgio Sisti, Melzo; Ermete Riva, Merate; Learco Sala, Monza, all of Italy

[73] Assignee: Carlo Erba Strumentazione S.p.A., Italy

[21] Appl. No.: 65,333

[22] Filed: Aug. 9, 1979

[30] Foreign Application Priority Data

Nov. 22, 1978 [IT] Italy .............................. 30052 A/78

[51] Int. Cl.³ .......................................... G01N 31/08
[52] U.S. Cl. ..................................... 73/23.1; 219/201
[58] Field of Search ......................... 73/23.1; 219/201

[56] References Cited
U.S. PATENT DOCUMENTS

| | | | |
|---|---|---|---|
| 3,385,099 | 5/1968 | Diem et al. | 73/23.1 |
| 3,403,545 | 10/1968 | Carter | 73/23.1 |
| 3,440,397 | 4/1969 | Vesper et al. | 73/23.1 X |
| 4,057,998 | 11/1977 | Moreau | 73/23.1 |
| 4,096,908 | 6/1978 | Lamy | 73/23.1 X |

Primary Examiner—Gerald Goldberg
Assistant Examiner—Joseph W. Roskos
Attorney, Agent, or Firm—Lerner, David, Littenberg & Samuel

[57] ABSTRACT

A gas chromatographic chamber in the form of an oven is disclosed, including an outer envelope including insulated walls defining the chromatographic chamber which can be made air tight, an inner housing section within that chamber for housing the chromatographic column, and including an air distributor to maintain the uniform distribution of air within the inner housing section, as well as a heater to heat the air therein, non-thermally insulating partitions within the chamber and spaced from the insulated wall to provide a pneumatically insulated space between the insulated walls and the inner housing section, and a fluid circulator to create the controlled circulation of fluid within the pneumatically insulated space to effect the temperature within the inner housing section.

9 Claims, 3 Drawing Figures

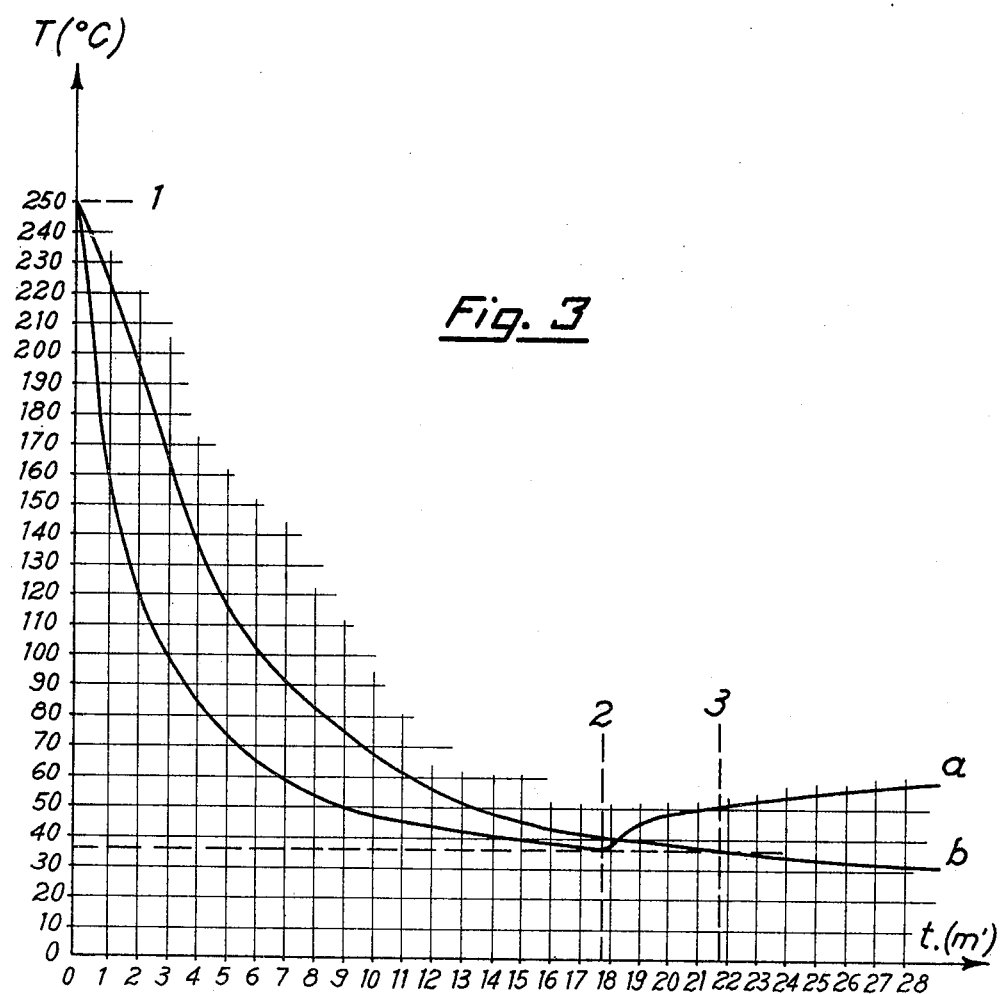

GAS CHROMATOGRAPHIC CHAMBER

BACKGROUND OF THE INVENTION

1. Field of the Invention

This invention concerns a chamber, or "oven", in which at least one gas cromatographic column is housed, said chamber being designed to be submitted to a predetermined program of temperature variations in order to obtain a suitable separation of the components of substances which pass through the column and have to be subject to analysis at the column outlet.

Generally speaking, this program of temperature variations includes an initial heating stage, a central stage in which thermal conditions are kept constant or changed according to a preset program, and finally a final cooling stage. The latter temperature may be either higher or lower than the ambient temperature and generally slightly exceeds it; the program, however, changes in function of different factors, among which mainly the nature of the analyzed substance.

2. Description of the Prior Art

To obtain these temperature programs, the gas chromatographic column is housed, as known, in a so called gas chromatographic chamber, essentially consisting of an envelope, for instance parallelepiped-on-shaped with insulated walls, airtight towards the outside so that the internal volume, where the gas chromatographic column in housed, is completely insulated from the outside. In this volume heating means are placed, for instance constituted by one or more resistors, as well as means performing the most possible uniform distribution of the air present inside the envelope and also of heat produced by said resistors, in order to bring all points of the envelope internal volume—and therefore all points of the columns housed in it—at the same preset temperature conditions. The above mentioned air and heat distribution means inside the gas chromatographic oven usually consist of a least one fan suitably positioned inside said close volume and placed in function of the heating resistor position. In this way, satisfactory results are obtained suitable for the operative needs when the chamber is heated, until it reaches the operative temperatures, and also when the chamber is kept at a constant or variable temperature during the central stage of the operative program.

The subsequent final cooling stage, on the contrary, as it is carried out in the gas chromatographic chambers known up to now, results in numerous disadvantages and drawbacks, for which no remedy has yet been found. In fact, in the most general case in which the final cooling temperature is slightly higher than the ambient one, the cooling operation in the known chambers is performed by opening towards the outside the chamber close volume, at least through two air locks which, also with the aid of the fan present within this volume, cause a circulation of external air, cooler than the internal one, until the latter reaches the desired values.

This operative method, necessarily deriving from the structure of the gas chromatographic chambers known up to now, besides involving a relative structural complication for the necessary use of the above mentioned air locks, which must ensure the hermetic closure of the chamber internal envelope and at the same time be insulated like all the chamber envelope walls, causes a first drawback related to the possibility of submitting the oven to thermal shocks risking to damage the chamber itself. In fact, cooling, according to the procedures followed up to now and previously indicated, cannot be performed under the optimal conditions required for this operation and for the others consisting in a temperature change obtained by always keeping at the same temperature all the points of the oven internal envelope and therefore the gas chromatographic column. On the contrary, the opening of said air locks, even if their position is suitably chosen, always involves the formation of preferential currents, which cause zones of lower temperature than the one of the remaining part of the envelope and therefore cause differential cooling in different zones of the gas chromatographic column.

Another drawback, perhaps even more serious than the previous one, consists in the necessity of considering a so called postcooling delay before performing a new cycle of temperature with the same gas chromatographic chamber. In fact, the air cooling inside the oven envelope may be obtained rather quickly using the system of the air locks, but anyway, when the air inside said envelope has reached the desired temperature of cycle end, it is not possible to start a new cycle, as the envelope walls, especially in the insulating layer, still keep heat absorbed during the preceding stage and this heat is gradually transmitted to the internal ambient, which cannot be closed to perform a new operative cycle until heat has not completely disappeared. This involves the necessity of keeping the oven in post-cooling conditions for a considerable time period, during which the chamber, of course, cannot be used.

The above mentioned drawbacks of the known gas chromatographic ovens, which occur when the cooling is carried out by means of ambient air, are even more marked when the cooling is obtained by other means, which should bring the cooling final temperature to lower values than the ambient one. Actually, in these cases, a gas at sub-ambient temperature is for instance introduced, which may even more easily provoke thermal shocks to the gas chromatographic column. Alternatively, it is possible to introduce air cooled by means of a refrigerating system, and in this case, too, there is the possibility of thermal shocks, besides the difficulty of realizing the refrigerating system (which must be a multi-stage one to prevent it may be damaged by excessively hot air treated at the beginning) and the difficulty in the refrigerating system operation, as the air volume treated is relatively high and therefore its cooling gives rise to a considerable condensate.

SUMMARY OF THE INVENTION

These and other disadvantages of the known systems are now avoided by means of the gas chromatographic chamber according to this invention, the objects of which are essentially to ensure a very uniform cooling of the oven internal ambient, in order to avoid thermal shocks to the gas chromatographic column and also to avoid the need of a post-cooling delay, which has always to be considered in the gas chromatographic chambers known up to now.

To achieve these and other objects the gas chromatohraphic chamber according to this invention, of the type consisting of an envelope with insulated walls defining a shutoff space which houses at least one gas chromatographic column and one or more elements for heating and/or uniformly distributing air inside this space, is essentially characterized in that it comprises, between the insulated wall internal surface and the gas chromatographic column housing, an hollow space pneumatically insulated from the housing space by means of non-thermally insulating separating septa, and pneumatically connected to at least a device to determine a controlled circulation of fluid inside that hollow space, captable of affecting the internal temperature of said space. Consequently, according to this invention, the gas chromatographic chamber internal volume is no longer openend to introduce ambient air, but it is cooled by means of a fluid current circulation, for instance a current of ambient air, lapping on the walls defining this internal space and which, thanks to the fan placed inside this internal space, allows to keep an almost absolutely uniform temperature, at any moment, on all the internal space surface. On the basis of the features of this cooling current, it is possible to obtain any temperature gradient during the cooling stage, while the period of post-cooling delay is no longer necessary as heat accumulated by the insulated parts of the oven walls is eliminated by the current circulating in the hollow space; this current may be maintained even after a new cycle has started, at least until the envelope internal temperature has reached the temperature value of the insulated external walls. In any case, the hollow space constitutes a thermal insulating space preventing heat from passing from the walls to the envelope internal volume.

BRIEF DESCRIPTION OF THE DRAWINGS

FIG. 3 represents two comparison graphs showing an identical program of temperatures in a conventional gas chromatographic chamber and i a gas chromatographic chamber according to the invention, respectively.

DESCRIPTION OF THE PREFERRED EMBODIMENTS

Figure 1:
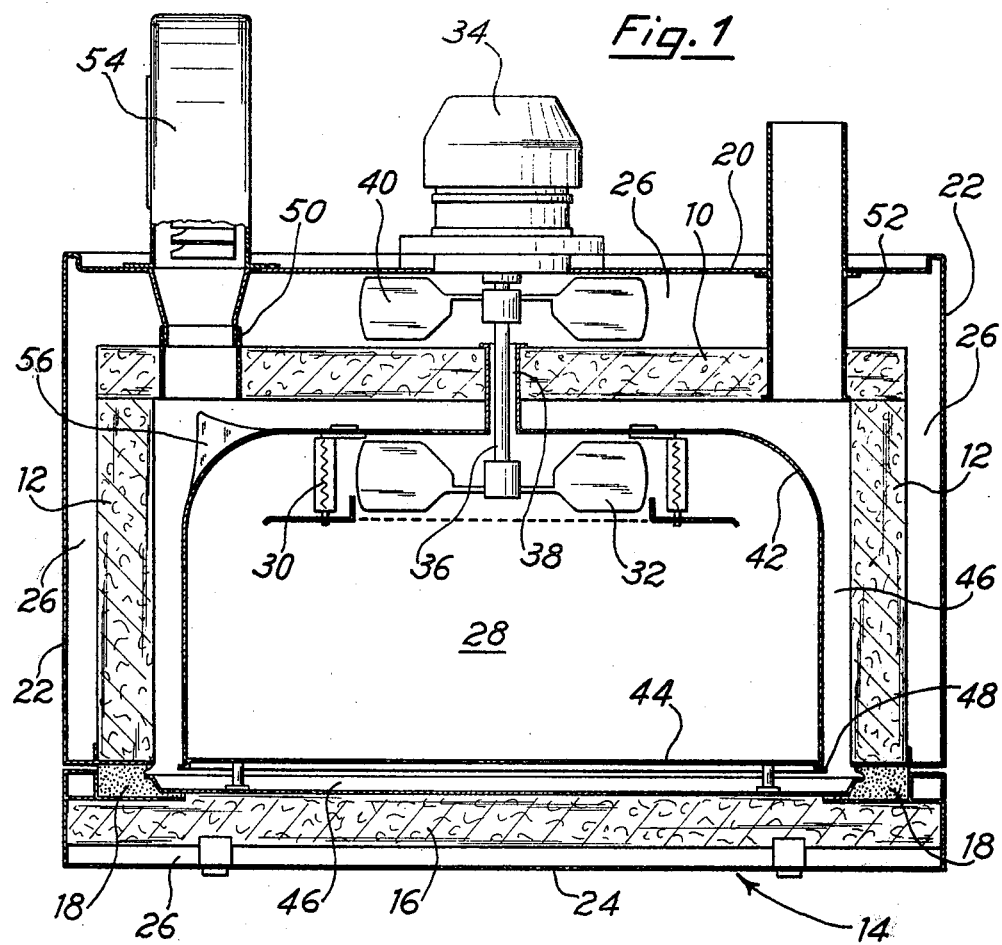
FIG. 1 is a cross section, according to a horizontal plane, of a gas chromatographic oven according to the invention.

First considering FIG. 1, the gas chromatographic chamber shown in it is substantially constituted by an envelope, for instance parallelepiped-on-shaped, defined as known by stationary insulated walls 10, 12 and by a door 14, which, too, has an insulating layer 16. The door 14, which may constitute the oven front part, can be fastened to the chamber body by means of any suitable closing system and its edge is provided with a closing and insulating gasket 18, in order to avoid any continuity solution between the insulated zones 12 and 16. Also in an already known way, between the insulated walls 10, 12 and 16 and the corresponding external walls 20, 22 and 24 surrounding the envelope, an hollow space 26, possibly opening towards outside in various points, is designed to form an insulating jacket essentially aimed at avoiding the risk of scalds or anyway of troubles to the operator touching these external parts when the oven is in operation.

These walls delimit an internal volume 28, which can be completely closed towards the outside and which houses the gas chromatographic column (not illustrated), connected to the outside by means of suitable fitting (not illustrated, too), generally positioned in the upper part, not visible in the figure, of the above mentioned envelope. The space or internal volume 28 contains heating means, for instance one or more electrical resistors, as diagrammatically shown at 30, as well as means to perform the most possible uniform temperature distribution inside this volume 28. In practice, the latter means consist of a fan 32, suitably positioned with respect to the resistors 30 and actuated by a motor 34 mounted on the external back wall 20. The shaft 36 of fan 32 by means of a support 38, airtightly crosses the insulated back wall 10 and may be fitted with another fan 40 causing air circulation in the hollow space 26, obviously improving the operative conditions.

In such a chamber, substantially in a known way, the internal volume 28 heating is performed by resistors 30 and simultaneously actuating fan 32, in order to obtain the most possible temperature uniformity, at any moment, on the whole volume of the space 28 and therefore of the column housed in it.

According to the invention, to achieve the above mentioned objects and particularly to carry out a better cooling stage and to have the possibility of immediately starting a new analytical cycle at the end of the preceding one, between the insulated walls 10, 13 and 16 and the internal space 28, a series of separating septa 42, 44 is provided, consisting of thermally conductive material, for example metal material, which all together pneumatically separate the internal space 28 from an internal hollow space 46, actually surrounding all the volume 28, not only in correspondence with its side walls, as shown in the figure, but also in the bottom and, at least partially, in the oven upper section. The hollow space 46 thus constituted extends also on the cover part, between wall 16 and septum 44, which is connected to septum 42 by means of a suitable gasket 48.

Two short tubular fittings 50 and 52 airtighlty cross the back walls 10 and 20 as well as the hollow space 26 existing between them, in order to pneumatically connect the internal hollow space 46 with the external ambient.

More exactly, fitting 50 is connected to a fan 54 capable of creating a current of air through the whole hollow space 46, the current being then discharged through fitting 52. Inside the hollow space 46 there may be baffles, for example as indicated at 56, to distribute in the most possible uniform way the cold current and thus avoiding extreme differences of temperature between various points of the septa 42 positioned in correspondence with the current inlet and outlet zones, respectively.

The passage of a suitable current of air through the hollow space 46 therefore enables to obtain uniform cooling of volume 28, especially if the fan 32 is kept working, avoiding any thermal shock to the column and obtaining any desired temperature gradient by suitably regulating fan 54. Once cooling is over, the temperature of volume 28 may be maintained at any desired value and, in particular, it is possible to compensate heat emission from the insulated zones 10, 12 and 16 by maintaining the above mentioned air flow in the hollow space 46 also at least during the initial stages of the oven new operative cycle, which can therefore be started immediately after cooling of the preceding cycle is over.

From what has been reported above, it becomes obvious that the control of the temperature conditions of volume 28 by means of the passage of a fluid current through the hollow space 46 can be performed at any temperature value, by suitably choosing the conditions of the current speed and the circulating fluid temperature. In particular, it will of course be possible to circulate hot gas to cooperate with resistors 30 or even to substitute them during the oven heating stage, or to circulate a gas at very low temperature, when there is a need for cooling down to lower temperatures than the ambient one and possibly even lower than 0° C.

Figure 2:
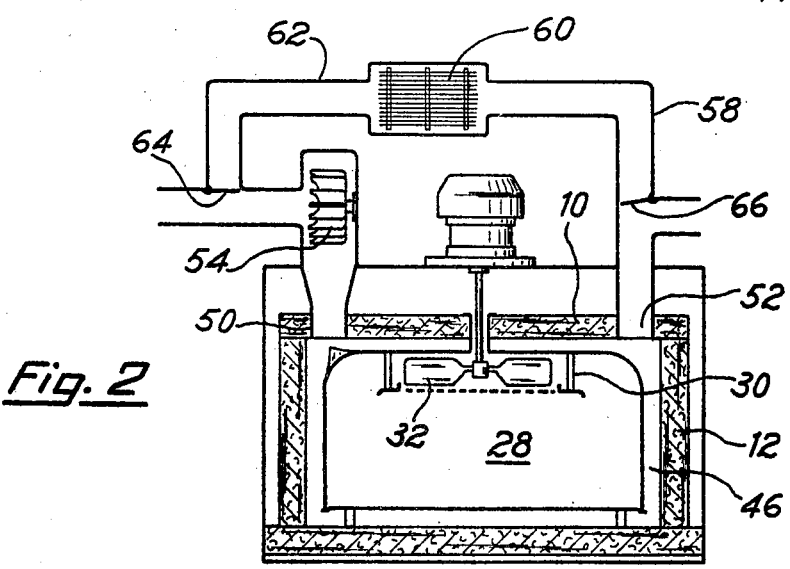
FIG. 2 is a diagram of the same oven of FIG. 1, when it is connected to a refrigerating system for cooling down to a temperature lower than the ambient one.

FIG. 2 diagrammatically shows a case where the above described gas chromatographic chamber is feeded with air colder than the ambient temperature. In this case, said fitting 52 is connected to a tube 58, which goes to the heat exchanger of a refrigerating unit 60, the outlet of which is connected, by means of a tube 62, to of suction of fan 54. In this way, air circulating in the hollow space 46 is cooled in close circuit and it is possible to use a single-stage refrigerating unit, as, even during cooling initial stages, the air going to the heat exchanger of unit 60 has a sufficiently low temperature not to damage the unit. Moreover, considering the low air volume treated in this close circuit, the condensate phenomena result to be limited and in any case do not affect the atmosphere of volume 28. A couple of valves or air locks 64 and 66 enables exclusion of the refrigerating unit, connecting the tubes 58 and 62 to the external ambient.

To prove the advantageous results achievable with a gas chromatographic oven according to this invention, comparison tests have been performed, carrying out a complete cycle of temperature changes in a conventional chamber and in a chamber according to the invention, respectively. The attached graph (FIG. 3) points out the difference between two cooling curves obtained with a conventional gas chromatographic chamber (curve a) and the new chamber with hollow space (curve b).

Point 1 indicates the beginning of the cooling period starting from a temperature of 250° C. For the conventional oven, the beginning of this period corresponds to the exclusion of heating resistors and the opening of the communication lock; for the chamber according to the invention, it corresponds to the exclusion of heating resistors and the actuation of the centrifugal fan blowing in air into the hollow space. The curve profile in the cooling initial period clearly shows a substantial difference of gradient, wich, for the chamber according to the invention, means lower stress to the columns housed in it.

In the conventional chamber, the closure of the communication lock occurs when a temperature of 36° C. is reached (10° C. more than the ambient temperature); from now on it is possible to perform an isotherm, provided that the temperature thereof exceeds 60° C., as it appears obviuos that heat restitution from the insulating material tends to increase the temperature above this value. The time necessary to reach the temperature of 36° C. is less than 18 minutes for the conventional chamber and 22 minutes for the new one, but considering that with the latter there is the possibility to maintain the hollow space ventilation even during the thermoregulation stage, it is possible to start the low isotherm period after 22 minutes, provided that the temperature thereof exceeds 36° C.

The relatively more time needed by new chamber to reach the cooling final temperature is widely compensated by the possibility of operating with lower initial temperature or by the possibility of starting in advance (namely without waiting to reach lower temperatures) the period of low isotherm.

For example, for an initial isotherm of 60° C., it is sufficient to suspend cooling at this temperature, with considerable time saving.

It is to be understood that the above described embodiment may undergo to many modifications without departing from the spirit and scope of this invention.

We claim:

1. A gas chromatographic chamber comprising an outer envelope including insulated wall members defining said chamber which may be closed in an air-tight manner, an inner housing section within said chamber, said inner housing section adapted to include at least one chromatographic column and including inner housing section air distribution means for maintaining a uniform distribution of the air within said inner housing section and inner housing section heating means for heating the air within said inner housing section, non-thermally insulating partition means within said chamber and spaced from said insulated wall members so as to provide a pneumatically insulated space between said insulated wall members and said inner housing section, said non-thermally insulating partition means defining said inner housing section, and circulation means for creating a controlled circulation of fluid within said pneumatically insulated space so as to affect the temperature within said inner housing section.

2. The gas chromatographic chamber of claim 1 including inlet duct and outlet duct means connected to said penumatically insulated space through said insulated wall members whereby a fluid may be circulated through said pneumatically insulated space from said inlet duct means to said outlet duct means.

3. The gas chromatographic chamber of claim 2 including baffle means located in said pneumatically insulated space for dividing said fluid being circulated through said pneumatically insulated space into a plurality of fluid currents.

4. The gas chromatographic chamber of claim 2 wherein said fluid comprises ambient air.

5. The gas chromatographic chamber of claim 2 wherein said fluid comprises a gas maintained at a temperature below ambient temperature.

6. The gas chromatographic chamber of claim 2 including conduit means for connecting said inlet duct means to said outlet duct means to create a closed circuit including said pneumatically insulated space, and including cooling means located in said closed circuit between said outlet duct means and said inlet duct means for cooling said fluid circulated therethrough.

7. The gas chromatographic chamber of claim 6 wherein said cooling means comprises a heat exchanger of a refrigeration system.

8. The gas chromatographic chamber of claim 7 wherein said conduit means includes opening means for selectively permitting connection of said conduit means with a source of air.

9. The gas chromatographic chamber of claim 8 including a plurality of said opening means.

* * * * *